United States Patent
Viertiö-Oja et al.

(10) Patent No.: US 7,599,735 B2
(45) Date of Patent: Oct. 6, 2009

(54) ELECTRODE CONFIGURATION FOR CENTRAL NERVOUS SYSTEM MONITORING

(75) Inventors: Hanna E. Viertiö-Oja, Espoo (FI); Timothy Sampson, Helsinki (FI)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/316,374

(22) Filed: Dec. 22, 2005

(65) Prior Publication Data

US 2007/0255164 A1    Nov. 1, 2007

(51) Int. Cl.
*A61B 5/04*    (2006.01)

(52) U.S. Cl. .............. 600/544; 600/545; 600/546; 600/383

(58) Field of Classification Search ............ 600/383, 600/544, 545, 546
See application file for complete search history.

(56) References Cited

U.S. PATENT DOCUMENTS

| | | | | |
|---|---|---|---|---|
| 4,171,696 | A | * | 10/1979 | John .................. 600/544 |
| 4,776,345 | A | * | 10/1988 | Cohen et al. ........... 600/544 |
| 6,032,065 | A | * | 2/2000 | Brown ................ 600/544 |
| 6,032,072 | A |   | 2/2000 | Greenwald et al. |
| 6,394,593 | B1 |  | 5/2002 | Komplin et al. |

(Continued)

FOREIGN PATENT DOCUMENTS

| | | |
|---|---|---|
| EP | 1 493 383 A2 | 1/2005 |
| EP | 1 516 581 A2 | 3/2005 |
| WO | 99/38437 A1 | 8/1999 |
| WO | 03/057030 A1 | 7/2003 |
| WO | 2004/028365 A2 | 4/2004 |

OTHER PUBLICATIONS

Croft, Rodney, et al. "EOG correction: A comparison of four methods." 2005. Psychophysiology, vol. 42 pp. 16-24.*

(Continued)

*Primary Examiner*—Max Hindenburg
*Assistant Examiner*—John Pani
(74) *Attorney, Agent, or Firm*—Andrus, Sceales, Starke & Sawall, LLP

(57) ABSTRACT

The invention relates to a method for positioning electrodes in an electrode array comprising a plurality of electrodes for central nervous system (CNS) monitoring from the forehead of a subject. In order to enable efficient detection of eye movement artifacts with a minimum number of electrodes, first and second electrodes are positioned so that eye movement in one of the horizontal or vertical directions causes a negligible overall voltage change between the first and second electrodes and at least a third electrode is positioned so that eye movement in the other of said horizontal and vertical directions causes a high potential difference between the third electrode and an auxiliary electrode, wherein the auxiliary electrode is one of the electrodes in a set comprising one of the first and second electrodes and a fourth electrode. The first and second electrodes are arranged to record an EEG signal and the third electrode and the auxiliary electrode are arranged to record an EOG signal indicative of eye movements of the subject.

10 Claims, 4 Drawing Sheets

U.S. PATENT DOCUMENTS

| | | | |
|---|---|---|---|
| 6,394,953 B1 | 5/2002 | Devlin et al. | |
| 6,934,570 B2 * | 8/2005 | Kiani et al. | 600/324 |
| 6,950,698 B2 | 9/2005 | Sarkela et al. | |
| 2005/0004489 A1 * | 1/2005 | Sarkela et al. | 600/544 |

OTHER PUBLICATIONS

Joyce, Carrie, et al. "Tracking eye fixations with electroocular and electroencephalographic recordings." 2002. Psychophysiology, vol. 39 pp. 607-618.*

Gratton, Gabrielle. "Dealing with artifacts: The EOG contamination of the event-related brain potential." 1998. Behavior Research Methods, Instruments, and Computers. 30(1) pp. 44-53.*

European Search Report dated May 7, 2007.

* cited by examiner

ELECTRODE CONFIGURATION FOR CENTRAL NERVOUS SYSTEM MONITORING

FIELD OF THE INVENTION

The present invention relates generally to positioning of electrodes in an electrode array comprising a plurality of electrodes for central nervous system monitoring from the forehead of a patient.

BACKGROUND OF THE INVENTION

Neuromonitoring is a subfield of clinical patient monitoring focused on measuring various aspects of brain function and on changes therein caused by neurological diseases, accidents, and drugs commonly used to induce and maintain anesthesia in an operation room or sedation in patients under critical or intensive care.

Electroencephalography (EEG) is a well-established method for assessing brain activity. When measurement electrodes are attached on the skin of the skull surface, the weak biopotential signals generated in brain cortex may be recorded and analyzed. The EEG has been in wide use for decades in basic research of the neural systems of the brain as well as in the clinical diagnosis of various central nervous system diseases and disorders.

The EEG signal represents the sum of excitatory and inhibitory potentials of large numbers of cortical pyramidal neurons, which are organized in columns. Each EEG electrode senses the average activity of several thousands of cortical pyramidal neurons.

The EEG signal is often divided into four different frequency bands: Delta (0.5-3.5 Hz), Theta (3.5-7.0 Hz), Alpha (7.0-13.0 Hz), and Beta (13.0-32.0 Hz). In an adult, Alpha waves are found during periods of wakefulness, and they may disappear entirely during sleep. Beta waves are recorded during periods of intense activation of the central nervous system. The lower frequency Theta and Delta waves reflect drowsiness and periods of deep sleep.

In clinical environment, the EEG measurement electrodes are often placed only onto the forehead of the patient, since a frontal cortex EEG is enough for most clinical applications and the forehead is a convenient measurement area from the point of view of both the patient and the nursing staff. Consequently, various electrode array systems have been developed for acquiring EEG signals from the frontal and temple areas of a patient. U.S. Pat. No. 6,394,953, for example, discloses a sensor comprising at least one measurement electrode on the forehead and at least one further electrode in the temple area of the patient.

In addition to brain waves, a surface EEG normally includes various other signal components, such as those caused by eye movements and eye blinks. The cornea of the eye is electrically positive relative to the retina and thus the eye forms an electrical dipole whose movements cause signal components to superpose onto the EEG signal. Although the eye movements and blinks that appear in an EEG signal contain information on the state of a patient, the said signal components are on the other hand considered as artifact that hampers the analysis of the brain waves. Therefore, in order to accomplish an accurate EEG analysis, eye movements/blinks need to be detected and their effect on the EEG removed.

For the detection, it is advantageous to measure the eye movements independently from the EEG signal as far as this is possible. FIG. 1 illustrates a straightforward method for detecting eye movements in all possible directions. Horizontal eye movements are detected by measuring the voltage difference between two electrodes A and B positioned on the opposite temple areas in line with the eyes. Vertical eye movements and blinks are detected by measuring the voltage difference between two further electrodes C and D positioned above and below one eye in line with the vertical axis 11 of the eye. A drawback related to this method is that the number of electrodes needed is rather high since two additional electrodes are needed for measuring the EEG (not shown in the figure).

However, some of these electrode array systems developed for acquiring EEG signals from the frontal and temple areas of a patient are designed for uncoupling the EEG signals, the electromyographic (EMG) signals, and the electro-oculographic (EOG) signals. U.S. Pat. No. 6,032,072, for example, discloses a sensor comprising one pair of closely positioned electrodes and at least one electrode widely spaced from the said pair. The idea behind this configuration is that a pair of closely positioned electrodes reflects primarily the EMG or EOG activity, while the voltage measured across a pair of well-spaced electrodes reflects primarily the EEG activity.

U.S. Pat. No. 6,950,698, in turn, discloses an electrode array comprising at least four measurement electrodes positioned on the forehead and possibly also in the temple area of the patient. In one embodiment, an electrode pair in the top part of the forehead is primarily sensitive to EEG signal, while another pair locating above the eyebrows is primarily sensitive to EMG and EOG activity.

A further drawback related to the current electrode array systems is that the detected EMG/EOG activity may lead to a considerable loss of collected information, since the contaminated EEG epochs need to be rejected.

The present invention seeks to alleviate or eliminate the above-mentioned drawbacks and to reduce the number of electrodes needed to detect eye movements in connection with EEG measurement.

SUMMARY OF THE INVENTION

The present invention seeks to provide an electrode positioning method and an electrode array for central nervous system (CNS) monitoring from the forehead of a patient, which improve the resistance of the monitoring channel against eye movement artifact. The present invention further seeks to provide a method and an electrode array which enable the amount of rejected data to be minimized and which enable both vertical and horizontal eye movements to be dealt with efficiently with a minimum number of electrodes.

In the present invention, two electrodes are positioned so that that eye movement in one of the vertical or horizontal directions causes a substantially zero potential difference between the said electrodes, and a third electrode is positioned so that eye movement in the other of said horizontal and vertical directions causes a high potential difference between the third electrode and an auxiliary electrode, which may be one of the said two electrodes or a fourth, optional electrode. Below, the said two electrodes are also termed EEG electrodes and the third electrode is termed an EOG electrode according to what is the primary signal component of the electrode. Thus, given that eye movements have two components, vertical and horizontal, the EEG electrodes are positioned so that the electric potential variations due to one component cause a substantially zero overall voltage change in the EEG channel, while the EOG electrodes are positioned so that the voltage measured between these electrodes is as high as possible for the other component to enable efficient detection of the eye movement artifacts possibly still appearing in the EEG channel. Since the electrode configuration makes the EEG signal resistant to the artifacts caused by eye movements in one of the two principal directions and since the EOG channel is further highly sensitive to eye movements in the other principal direction, eye movement and blink artifacts can be removed efficiently from the EEG signal.

Thus one aspect of the invention is providing a method for positioning electrodes in an electrode array comprising a plurality of electrodes for central nervous system (CNS) monitoring from the forehead of a subject. The method includes the steps of positioning first and second electrodes so that eye movement in one of the horizontal or vertical directions causes a negligible overall voltage change between the first and second electrodes and positioning at least a third electrode so that eye movement in the other of said horizontal and vertical directions causes a high potential difference between the third electrode and an auxiliary electrode, the auxiliary electrode being one of the electrodes in a set comprising the first electrode, the second electrode, and an optional fourth electrode, wherein the first and second electrodes are arranged to record an EEG signal and the third electrode and the auxiliary electrode are arranged to record an EOG signal indicative of eye movements of the subject.

Another aspect of the invention is that of providing an electrode array for acquiring electrical biopotential signals from the skin surface of a subject. The electrode array includes a single substrate attachable onto the skin of the subject, the substrate forming a strip-like structure comprising a first end and a second end, a first EOG electrode positioned on the substrate at the first end of the strip-like structure, a first EEG electrode positioned on the substrate at the second end of the strip-like structure, and a second EEG electrode positioned on the substrate so that the distance between the first EEG electrode and the second EEG electrode is at least as long as the distance between the first EOG electrode and the second EEG electrode, wherein the first EEG electrode and the second EEG electrode are arranged for recording an EEG signal and the first EOG electrode and the first EEG electrode are arranged for recording an EOG signal indicative of eye movements of the subject.

The present invention enables the monitoring channel to remain highly resistant against artifacts even when increased correlation between EEG patterns and eye movement artifacts may exist. Furthermore, the EEG channel suffers less and thus remains more robust in presence of artifact. This is due to the fact that the artifact-contaminated periods of the monitoring channel remain shorter since the EEG channel is sensitive to eye movements in one direction only. Consequently, the amount of the EEG channel data that needs to be rejected remains smaller. This enables sufficient data to be collected in a relatively shorter time period, which in turn adds to the speed of the measurement.

A further advantage of the invention is that the eye movements may be taken into account with a minimum number of electrodes. At minimum, the number of measuring electrodes is three although both horizontal and vertical eye movement artifacts are dealt with simultaneously with an EEG measurement.

Other features and advantages of the invention will become apparent by reference to the following detailed description and accompanying drawings.

BRIEF DESCRIPTION OF THE DRAWINGS

In the appended drawings, an EOG electrode is denoted with a single unfilled circle, an EEG electrode with two co-centric circles, and a combined EEG/EOG electrode with a circle filled with oblique lines. In the following, the invention and its preferred embodiments are described more closely with reference to the examples shown in FIG. 2 to 8 in the said drawings, wherein.

DETAILED DESCRIPTION OF THE INVENTION

Figure 1:
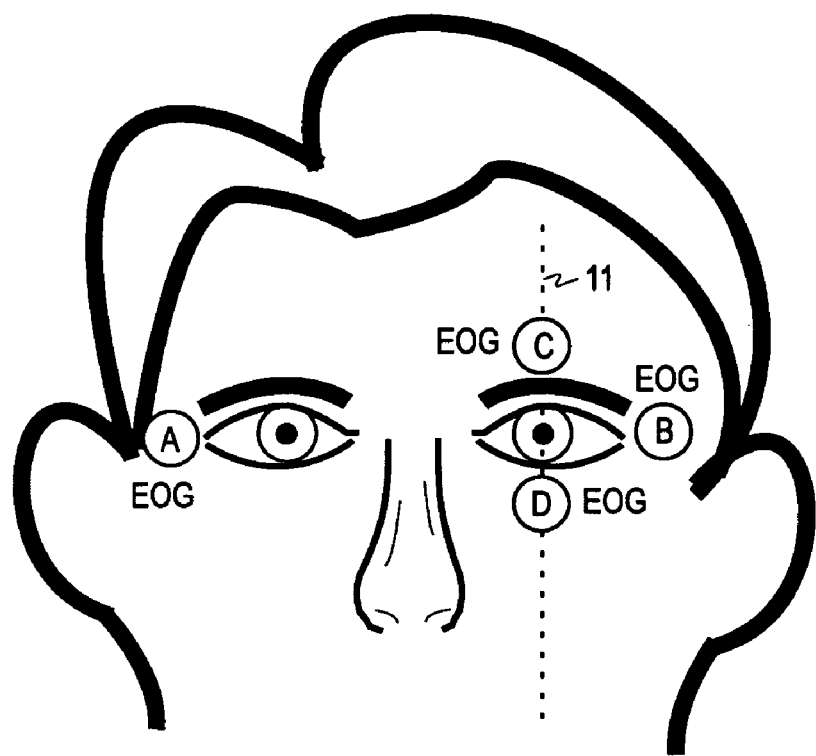
FIG. 1 is a frontal view of a human head illustrating a prior art mechanism for detecting eye movements.
Figure 2:
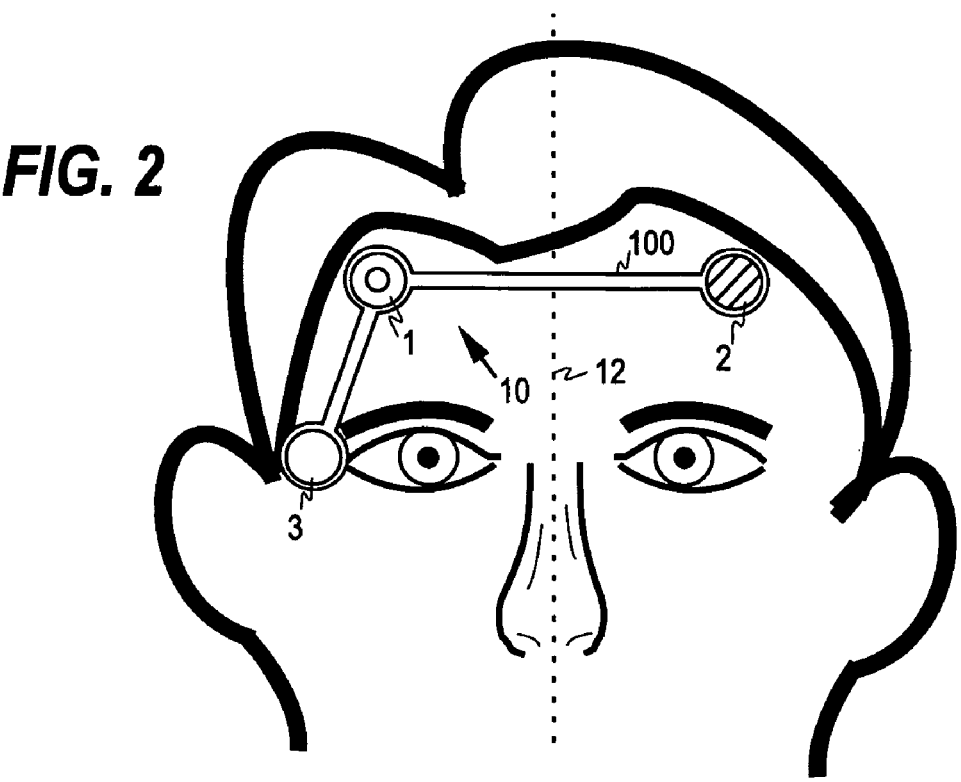
FIG. 2 illustrates one embodiment of the electrode configuration of the invention.

FIG. 2 illustrates one embodiment of an electrode array 10 according to the present invention. The electrode array comprises three measurement electrodes 1 to 3 of which the first and second electrodes are for measuring the EEG signal and the third and second electrodes for measuring the EOG signal.

The first electrode 1 is positioned onto the hairless front-lateral area of the frontal lobe of the patient, preferably as far as possible from the eye. The measurement electrode 2 is positioned similarly as the first measurement electrode, but on the opposite cortical hemisphere of the patient. Furthermore, the first and second electrodes are positioned substantially horizontally (i.e. in the same horizontal line) and at substantially equal distances from the vertical center axis 12 of the face, i.e. the second measurement electrode is positioned onto the spot which is the mirror image of the spot of the first measurement electrode, and vice versa, the vertical center axis being the mirror axis.

The EEG signal is measured from the measurement electrodes 1 and 2. Due to the symmetrical positions of the electrodes, the potential changes caused by vertical eye movements are substantially the same at both electrodes (assuming that the eyes move similarly to each other, as is the case normally). In other words, the potential changes caused by vertical eye movements tend to cancel in the EEG signal representing the voltage difference of the electrodes. The same applies to artifacts caused by blinks of the eyelids. Thus, the EEG channel is in this case resistant to artifact caused by vertical eye movements, but remains sensitive to artifacts caused by horizontal eye movements. In the embodiment of FIG. 2, the third measurement electrode 3 and one of the first and second measurement electrodes is used for measuring the EOG signal. For this purpose, the third measurement electrode is positioned so that the EOG voltage measured between this electrode and one of the first and second electrodes is as high as possible in case of horizontal movement of the eyes. In the example of FIG. 2, the said one electrode is measurement electrode 2, i.e. the EOG voltage is measured between electrodes 3 and 2. Therefore, the third measurement electrode is positioned on the temple of the patient, on the hemisphere opposite to that of measurement electrode 2. The temple here refers to the area between an eye and the ear on the same hemisphere as the eye. As to their internal structure, the electrodes may be similar to each other.

Figure 3:
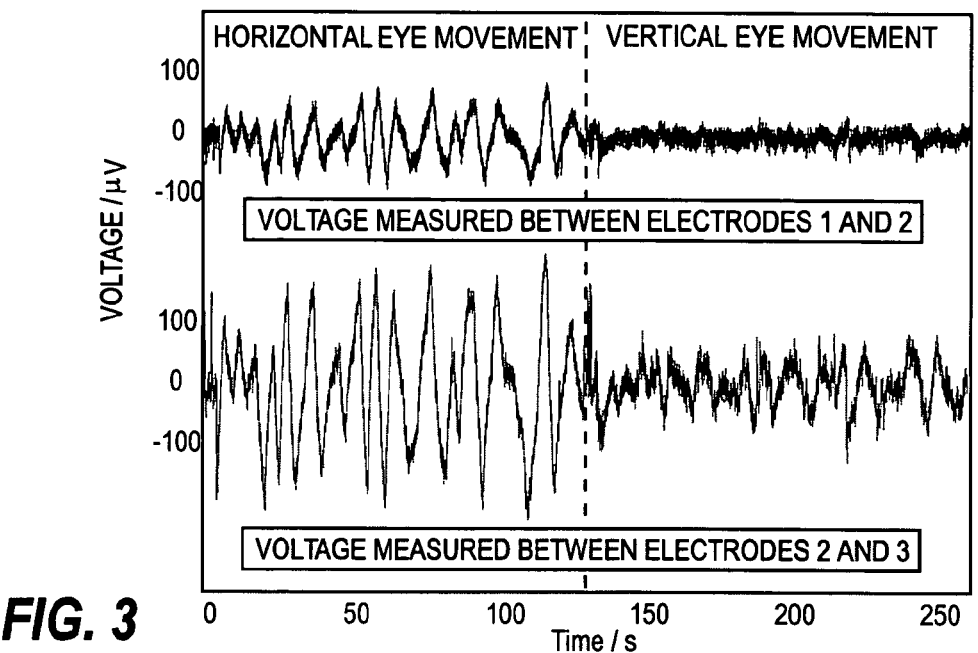
FIG. 3 illustrates an example of signals measured from the electrode configuration of FIG. 2.

FIG. 3 shows an example of the EEG and EOG signals measured by the electrode configuration of FIG. 2. The upper signal is the EEG signal measured between electrodes 1 and 2 and the lower signal is the EOG signal measured between electrodes 3 and 2. As can be seen from the figure, the EEG channel is sensitive to horizontal eye movement, but resistant to vertical eye movement, while the amplitude of the EOG signal is high for the horizontal movement, allowing efficient detection of the artifact caused by horizontal eye movement in the EEG signal.

Figure 4:
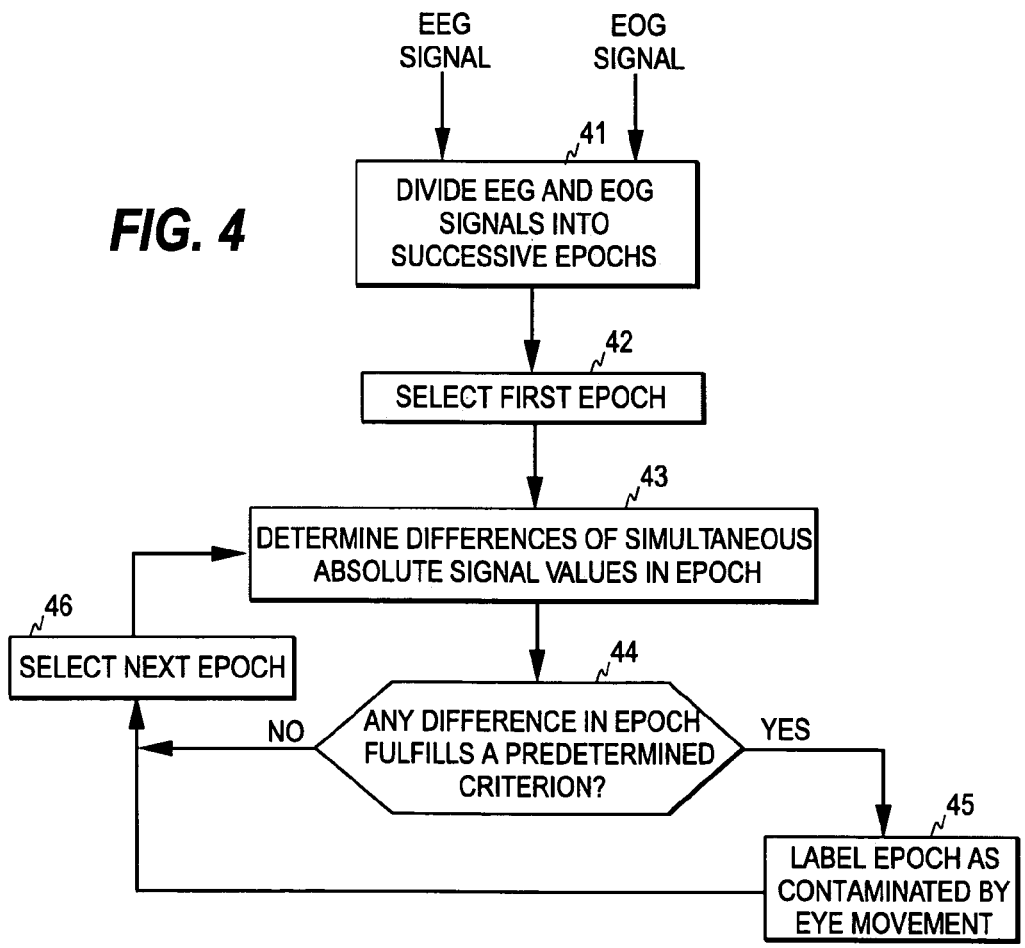
FIG. 4 is a flow diagram illustrating one embodiment of the method for detecting eye movement artifacts in connection with the electrode array of FIG. 2.

FIG. 4 illustrates one embodiment of a method for detecting eye movement artifact in connection with the electrode array of FIG. 2. As noted above, the EEG signal is measured between electrodes 1 and 2, whereas the EOG signal is measured between electrodes 3 and 2. First, the EEG and EOG channel signals are divided into successive epochs (step 41). It is assumed in this example that the length of each epoch is one second and that each epoch contains 200 samples, i.e. the sampling frequency is 200 Hz. For each epoch, the process then compares the two signals for example by determining the difference of the absolute values of simultaneous signal values. This may be done for each sample in an epoch. Assuming that the said signal values are $S_{EEG}(t_i)$ and $S_{EOG}(t_i)$, the process thus determines the difference $|S_{EOG}(t_i)|-|S_{EEG}(t_i)|$ for each sample $t_i$ within an epoch. The process then examines whether any of the differences fulfills a predetermined criterion indicative of the presence of eye movement (step 44). In this example, the process examines whether any of the differences exceeds a predetermined threshold value, such as 30 µV. If this is the case, the epoch is flagged to indicate that it is contaminated by eye movement artifact (step 45). Various other techniques may also be used to test whether at least a predetermined number of the samples of an epoch fulfill the criterion indicative of the presence of artifact.

Above, the EEG electrode pair is thus positioned so that the eye movement in the vertical direction causes a substantially zero overall potential difference between the EEG electrodes 1 and 2. Additionally, electrode 3 is positioned so that eye movement in the horizontal direction causes a high potential difference between electrodes 3 and 2, which act as the EOG electrodes. However, as discussed below, the electrode array may also be configured so that the roles of the horizontal and vertical directions are reversed. Furthermore, a fourth electrode may be provided for measuring the EOG channel, and the electrode array may be provided with a ground electrode.

The electrode array of the invention comprises at least three electrodes. Two electrodes, i.e. the EEG electrodes, are positioned so that that eye movement in one of the vertical or horizontal directions causes a negligible (i.e. a substantially zero) overall voltage change in the EEG signal measured between the said electrodes, while the third electrode, i.e. the EOG electrode, is positioned so that eye movement in the other of said horizontal and vertical directions causes a maximally high voltage (potential difference) between the third electrode and an auxiliary electrode, which is either one of the EEG electrodes or a fourth electrode positioned near the eye of the patient.

Figure 5:
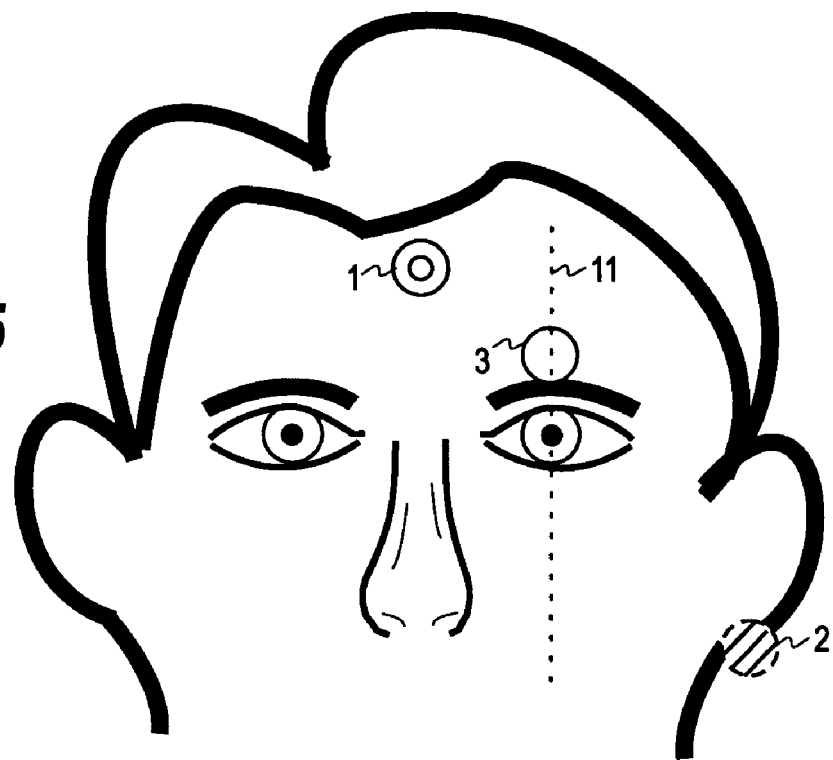
FIG. 5 illustrates a further embodiment of the electrode configuration of the invention.

FIG. 5 illustrates one embodiment of the invention, in which the roles of the principal directions are reversed from those of the embodiment of FIG. 2. In the embodiment of FIG. 5, the first electrode 1 is positioned symmetrically with respect to the eyes onto the forehead of the patient, preferably as far as possible from the eyes. The first electrode thus lies on the vertical center axis 12 of the face. The second measurement electrode 2 is positioned on the mastoid behind the ear of the patient, whereas the third electrode 3 is positioned directly above the eyebrow. In this example, the third electrode is positioned on the same hemisphere as the second electrode and in line with the vertical axis 11 of the eye. However, the third electrode may also be positioned on the opposite hemisphere with respect to the second electrode 2. As the second electrode is behind the ear on the mastoid, it is denoted with a dashed line in the figure.

In this case the potential changes caused by horizontal movement of the right and left eye balls tend to cancel each other due to the symmetric location of the electrode. In other words, due to the location of the electrode, the potential change caused by the horizontal movement of one eye at electrode 1 is opposite to the respective potential change caused by the other eye (assuming that the eye balls move similarly). Furthermore, horizontal eye movement does not cause any substantial potential change at the second electrode located on the mastoid, and therefore the horizontal eye movements tend to get cancelled in the EEG signal representing the voltage between electrodes 1 and 2. The voltage measured between the third electrode and electrode 2 is in this embodiment maximally high for vertical eye movements and blinks, thus allowing effective detection of the respective artifact in the EEG signal. A method according to FIG. 4 may be used for detecting the artifact caused by eye movements.

Figure 6:
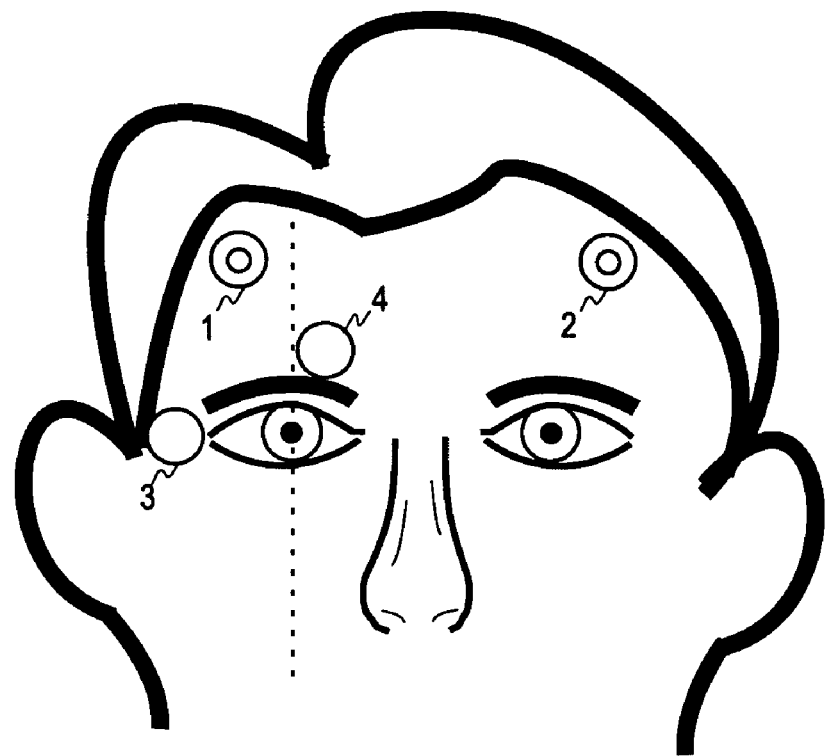
FIG. 6 illustrates an embodiment in which the electrode configuration of FIG. 2 is provided with dedicated electrodes for the EOG channel.

As discussed above, one of the EOG electrodes may be a combined EEG/EOG electrode. However, the electrode array may also comprise a dedicated EOG electrode pair. FIG. 6 illustrates a four-electrode configuration comprising an additional EOG electrode 4 as compared to the embodiment of FIG. 2. The fourth electrode is positioned directly above the eyebrow on the same hemisphere as electrode 3 and preferentially on the opposite side of the vertical axis of the eye with respect to electrode 3. In this embodiment, the EEG signal is measured between electrodes 1 and 2 as in the embodiment of FIG. 2, but the EOG signal is now measured between electrodes 3 and 4. As in the embodiment of FIG. 2, the EOG voltage is high for horizontal eye movements, while the EEG channel is resistant to vertical eye movements and remains sensitive to horizontal eye movements.

Figure 7:
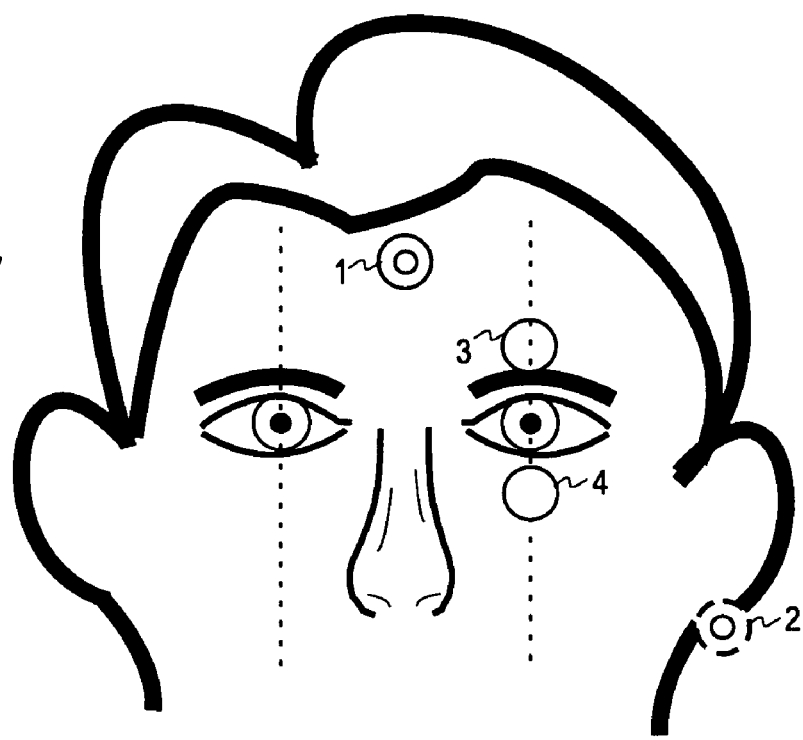
FIG. 7 illustrates an embodiment in which the electrode configuration of FIG. 5 is provided with dedicated electrodes for the EOG channel.

FIG. 7 illustrates a four-electrode configuration comprising an additional EOG electrode 4 as compared to the embodiment of FIG. 5. The fourth electrode is positioned directly below the same eye above which the third electrode is, so that the electrodes are substantially in line with the vertical axis 12 of the eye. As in the embodiment of FIG. 5, the EEG signal is measured between electrodes 1 and 2, whereas the EOG signal is now measured between electrodes 3 and 4. The EOG voltage is maximally high in case of vertical eye movements, and the EEG channel is resistant to horizontal eye movements.

Figure 8:
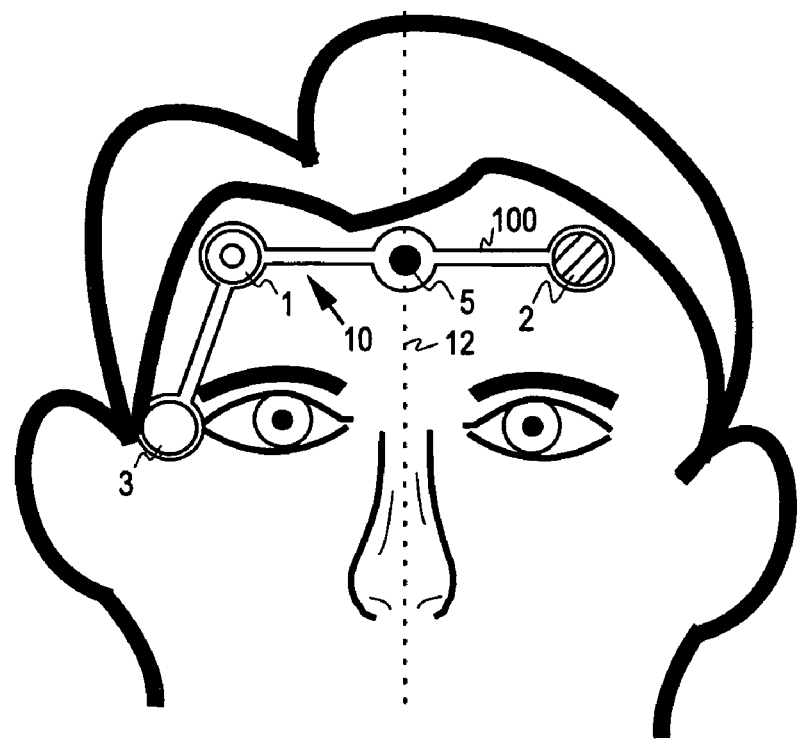
FIG. 8 illustrates a further embodiment of the electrode configuration of the invention.

Additionally, a ground electrode (GND) providing a common ground potential (0V) for the channels may be positioned to any location. FIG. 8 illustrates the electrode array of FIG. 2 provided with a ground electrode 5 positioned between the EEG electrodes 1 and 2.

As obvious from the above, the electrode array may comprise distinct electrodes or two or more of the electrodes may be mounted on a thin and flexible substrate made of plastic material, for example. FIGS. 2 and 8 show three and respectively four electrodes integrated onto the surface of a strip-like substrate 100 comprising two portions; a first portion between electrode 3 and electrode 1 and a second portion between electrode 1 and electrode 2. The first portion may be slightly shorter than or substantially as long as the second portion to enable the electrodes to be positioned in the above-described manner. For example, the length of the first portion may be about 8 cm and that of the second portion about 10 cm. The first portion may be set to an angle relative to the second portion, as is shown in FIGS. 2 and 8. The angle may be, for example, about 130 degrees. Furthermore, the second portion may be provided with a mark indicating the center line between electrodes 1 and 2, whereby the nursing staff may align the said mark with the vertical center line of the face. Alternatively, the ground electrode may indicate the center line between electrodes 1 and 2, as is shown in the embodiment of FIG. 8. In this case the electrode array may be attached to the patient by first attaching the ground electrode onto the vertical center line of the face. Each electrode of the array is further provided with a respective connector connecting the electrode to a terminal (not shown) normally manufactured to the free end of the strip-like substrate. The terminal may be connected with a mating terminal at the end of a measurement cable (not shown) connected to the amplifier state of the measuring apparatus. The connectors may be printed on the substrate.

Although the invention was described above with reference to the examples shown in the appended drawings, it is obvious that the invention is not limited to these, but may be modified by those skilled in the art without departing from the scope of the invention.

The invention claimed is:

1. A method to minimize a number of electrodes in an array to only three by positioning electrodes of the electrode array to identify, in an electroencephalographic (EEG) signal obtained by the array, time periods that are contaminated with artifacts resulting from eye movements of a subject, the method comprising steps of:
    positioning first and second electrodes of the array on a forehead of the subject at first and second locations at which the electrodes obtain the EEG signal including an electrooculographic (EOG) artifact, the EEG signal comprising a voltage difference between a voltage obtained at the first electrode and a voltage obtained at the second electrode, wherein the locations of the first and second electrodes are such that eye movement in one of a horizontal or a vertical direction will result in a minimal overall change in the voltage difference between the first electrode and the second electrode to provide the EEG signal in which artifacts resulting from eye movement in the one direction are minimized or eliminated;
    positioning a third electrode of the array on the head of the subject at a third location to maximize voltage changes occurring in an electrooculographic (EOG) signal as a result of eye movement in the other of the horizontal or the vertical direction obtaining the EOG signal, wherein the EOG signal comprises a voltage difference between a voltage obtained at the third electrode and a voltage obtained at an auxiliary electrode, wherein the auxiliary electrode is one of the electrodes in a set comprising the first electrode and the second electrode; and
    identifying time periods in which maximized voltage changes occur in the EOG signal as artifact contaminated time periods in the EEG signal wherein the maximized voltage changes result from eye movement in the other direction.

2. A method according to claim 1, wherein the positioning steps include
    positioning the first electrode on the front-lateral area of one of the hemispheres of a frontal lobe of the subject;
    positioning the second electrode on the front-lateral area of the frontal lobe of the subject at the opposite hemisphere when compared to the first electrode so that the first and second electrodes locate substantially symmetrically with respect to the eyes of the subject; and
    positioning the third electrode to the temple of the subject.

3. A method according to claim 1, wherein the positioning steps include positioning the third electrode on a temple of the subject, in which the temple is the area between an eye and an ear, the area being substantially at eye level anterior of the ear.

4. A method according to claim 1, further comprising the steps of:
    comparing the EEG signal and EOG signals with each other; and
    identifying artifact-contaminated time periods of the EEG signal based on the comparing step.

5. A method according to claim 4, wherein
    the comparing step includes the sub-steps of dividing the EEG signal and the EOG signal into successive epochs, each epoch comprising a certain number of signal values, determining differences of simultaneous absolute signal values within each epoch, and examining the differences within each epoch; and
    the identifying step includes a sub-step of flagging a respective epoch of the EEG signal as contaminated by eye movement, when at least a predetermined number of the differences in a corresponding epoch of the EOG signal fulfill a predetermined criterion.

6. A method according to claim 5, wherein the examining sub-step includes a sub-step of comparing the differences with a predetermined threshold value.

7. A method for positioning electrodes of an electrode array comprising not more than three measurement electrodes to identify, in an electroencephalographic (EEG) signal produced by the array, a period of time that is contaminated with artifacts resulting from eye movements of a subject, the method comprising steps of:
    positioning a first electrode of the array at a first location on a head of the subject and positioning a second electrode of the array at a second location on the head of the subject;
    obtaining an electroencephalographic (EEG) signal, the EEG signal comprising a voltage difference between a voltage obtained at the first electrode and a voltage obtained at the second electrode, wherein the locations of the first electrode and the second electrode are such that eye movement in a first direction selected from a group consisting of a horizontal direction and a vertical direction results in minimal change in the voltage difference, wherein the obtained EEG signal has minimal artifacts resulting from eye movement in the first direction;
    positioning a third electrode of the array at a third location on the head of the subject; obtaining an electrooculographic (EOG) signal comprising a voltage difference between a voltage obtained at the third electrode and the voltage obtained at the second electrode, wherein the location of the third electrode results in maximized voltage in the EOG signal as a result of eye movement in a second direction of the group consisting of the horizontal direction and the vertical direction; and
    using the maximized voltage changes in the EOG signal to identify a time period in the EEG signal as an artifact contaminated time period resulting from eye movement in the second direction.

8. The method of claim 7, further comprising:
    positioning a ground electrode on the head of the subject; and
    providing a common ground potential to the EEG signal and the EOG signal.

9. A method to minimize a number of electrodes in an array to only three by positioning electrodes of the electrode array to identify, in an electroencephalographic (EEG) signal obtained by the array, time periods that are contaminated with artifacts resulting from eye movements of a subject, the method comprising the steps of:

positioning first and second electrodes of the array on a forehead of the subject at first and second locations at which the electrodes will obtain the EEG signal;

obtaining the EEG signal by measuring a voltage difference between a voltage obtained at the first electrode and a voltage obtained at the second electrode, wherein the locations of the first and second electrodes are such that eye movement in one of a horizontal or a vertical direction will result in a minimal change in the voltage difference between the first electrode and the second electrode to provide the EEG signal in which artifacts resulting from eye movement in the one direction are minimized or eliminated;

positioning a third electrode of the array on the head of the subject at a third location to maximize voltage changes occurring in an electrooculographic (EOG) signal as a result of eye movement in the other of the horizontal or the vertical direction;

obtaining the EOG signal by measuring a voltage difference between a voltage obtained at the third electrode and a voltage obtained at an auxiliary electrode, wherein the auxiliary electrode is one of the electrodes in a set consisting of the first electrode and the second electrode; and identifying time periods in which the maximized voltage changes occur in the EOG signal as artifact contaminated time periods in the EEG signal wherein the maximized voltage changes result from eye movement in the other direction.

10. The method of claim 9 wherein the first electrode is placed at the first location on a first hemisphere of the head of the subject;

the second electrode is placed at the second location on a second hemisphere of the head of the subject;

the third electrode is placed at the third location on the first hemisphere of the head of the subject; and the auxiliary electrode is the second electrode, the EOG signal comprising the voltage difference between the third electrode and the second electrode.

* * * * *